(12) United States Patent
Ben-Cnaan et al.

(10) Patent No.: US 6,966,881 B2
(45) Date of Patent: Nov. 22, 2005

(54) CERVICAL DILATION MONITOR (76) Inventors: Miki Ben-Cnaan, 29 Borochov Street, Tel Aviv (IL); Ilan Halevi, 28 Biyalik st., Kadima (IL); Barak Halevi, 12 Keshet Street, Nes Tsiona (IL)

( * ) Notice: Subject to any disclaimer, the term of this patent is extended or adjusted under 35 U.S.C. 154(b) by 90 days.

(21) Appl. No.: 10/430,297

(22) Filed: May 7, 2003

(65) Prior Publication Data
US 2004/0225235 A1 Nov. 11, 2004

(51) Int. Cl.7 .......................... A61B 5/103; A61B 5/117
(52) U.S. Cl. ..................... 600/591; 600/588; 33/542
(58) Field of Search .............................. 600/587, 588, 600/591; 128/830; 33/511, 512, 542, 558, 33/783, 787, 806, 807, 542.1

(56) References Cited

U.S. PATENT DOCUMENTS

| | | | |
|---|---|---|---|
| 2,083,373 A | * | 6/1937 | Hardesty et al. ............... 33/806 |
| 2,924,220 A | * | 2/1960 | Von Micsky ............... 600/588 |
| 4,141,345 A | | 2/1979 | Allen et al. |
| 4,224,951 A | | 9/1980 | Hasson |
| 4,476,871 A | | 10/1984 | Hon |
| 4,489,732 A | | 12/1984 | Hasson |
| 4,611,603 A | * | 9/1986 | Kelso et al. ............... 600/588 |
| 5,658,295 A | | 8/1997 | Krementsov |
| 5,807,281 A | | 9/1998 | Welch |
| 6,039,701 A | * | 3/2000 | Sliwa et al. ............... 600/588 |
| 6,423,000 B1 | | 7/2002 | Berry |
| 6,524,259 B2 | | 2/2003 | Baxter-Jones et al. |

* cited by examiner

*Primary Examiner*—Max F. Hindenburg
*Assistant Examiner*—Jonathan Foreman
(74) *Attorney, Agent, or Firm*—Mark M. Friedman (57) ABSTRACT

A system for measuring dilation of a cervix of a uterus of a female during the first stage of labor, including an expandable gripping arrangement having two oppositely facing gripping members configured, such that, the gripping arrangement grips the dilating cervix. The system also includes a first elongated element having a calibrated scale disposed thereon and a second elongated element. A part of the second elongated element is disposed along the calibrated scale. The part of the second elongated element has an indicator disposed thereon. The first and second elongated element are mechanically connected to the gripping arrangement, in a manner such that, as the gripping arrangement expands with the dilating cervix, relative linear movement is generated between the first and second elongated elements, thereby moving the indicator with respect to the calibrated scale so as to give a measurement of dilation of the cervix.

15 Claims, 11 Drawing Sheets

CERVICAL DILATION MONITOR

FIELD AND BACKGROUND OF THE INVENTION

The present invention relates to a medical instrument and, in particular it concerns a cervical dilation monitor.

By way of introduction, it is still standard practice for the obstetrician to resort to regular vaginal examination in order to estimate cervical dilation and thereby assess the progress of labor during the first stage of active labor. The cervix dilates to about 10 cm during this stage of labor as well as effacing to a very thin layer. However, these examinations are uncomfortable to the patient, inaccurate, objective, as well as risking introducing infection into the uterus, these disadvantages being amplified if serial examinations are carried out by different observers.

Of relevance to the present invention is U.S. Pat. No. 5,658,295 to Krementsov which teaches an instrument, similar to calipers, with a scale for indicating dilation. The device taught by Krementsov is not designed to be left in position for continual monitoring. Additionally, the instrument is not disposable and requires repeated sterilization.

Of most relevance to the present invention is U.S. Pat. No. 4,141,345 to Allen et al. which teaches an expandable V-shaped caliper instrument. The dilation is measured using strain gauges. A shortcoming of the aforementioned system is that the system is not disposable and requires repeated sterilization.

Also of relevance to the present invention is U.S. Pat. Nos. 4,476,871 to Hon and 6,423,000 to Berry. Both of these patents teach systems for monitoring cervical dilation. However, both of the systems are non-disposable, expensive as well as intrusive to the patient.

There is therefore a need for a cheap, disposable cervical dilation monitor which is easy to fit and is comfortable and safe for the patient, takes into account cervical effacement, as well as providing accurate, continuous and objective measurements of cervical dilation.

SUMMARY OF THE INVENTION

The present invention is a cervical dilation monitor construction and method of operation thereof.

According to the teachings of the present invention there is provided, a system for measuring dilation of a cervix of a uterus of a female during the first stage of labor, comprising: (a) an expandable gripping arrangement having two oppositely facing gripping members and an outwardly biased restoring member, the gripping arrangement being configured, such that, the restoring member pushes the gripping members apart so that the gripping arrangement grips the cervix while the cervix dilates; (b) a first elongated element having a calibrated scale disposed thereon, and (c) a second elongated element, a part of the second elongated element being disposed along the calibrated scale, the part of the second elongated element having an indicator disposed thereon, the first elongated element and the second elongated element being mechanically connected to the gripping arrangement, in a manner such that, as the gripping arrangement expands with the dilating cervix, relative linear movement is generated between the first elongated element and the part of the second elongated element, thereby moving the indicator with respect to the calibrated scale so as to give a measurement of dilation of the cervix.

According to a further feature of the present invention, the second elongated element is a line.

According to a further feature of the present invention, at least one of the gripping members is expandable in order to grip a portion of the cervix while the cervix effaces.

According to a further feature of the present invention, there is also provided an insertion arrangement configured to keep the gripping members expanded during fitting of the gripping arrangement on the cervix.

According to a further feature of the present invention: (a) the first elongated element is hollow; and (b) the insertion arrangement is partially disposed within the first elongated element.

According to a further feature of the present invention, the gripping arrangement includes two flexible connecting elements, each of the connecting elements uniquely mechanically connecting one of the gripping members to the restoring member.

According to a further feature of the present invention: (a) the first elongated element is hollow and has a portion which is translucent, the portion including the calibrated scale; and (b) the part of the second elongated element is disposed within the first elongated element.

According to a further feature of the present invention: (a) the first elongated element is hollow; (b) the first elongated element has a first end and second end; (c) the first end is mechanically connected to the restoring member; and (d) the second elongated element extends substantially from the first end to the second end.

According to a further feature of the present invention, the second elongated element has a control element disposed thereon, the control element being configured to enable an operator move the second elongated element to contract the expandable gripping arrangement for fitting into the cervix.

According to a further feature of the present invention, the second elongated element is mechanically connected to the restoring member and one of the gripping members.

According to a further feature of the present invention, the second elongated element is mechanically connected to both of the gripping members.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a cervical dilation monitor construction and method of operation thereof.

The principles and operation of a cervical dilation monitor according to the present invention may be better understood with reference to the drawings and the accompanying description.

Figure 1:
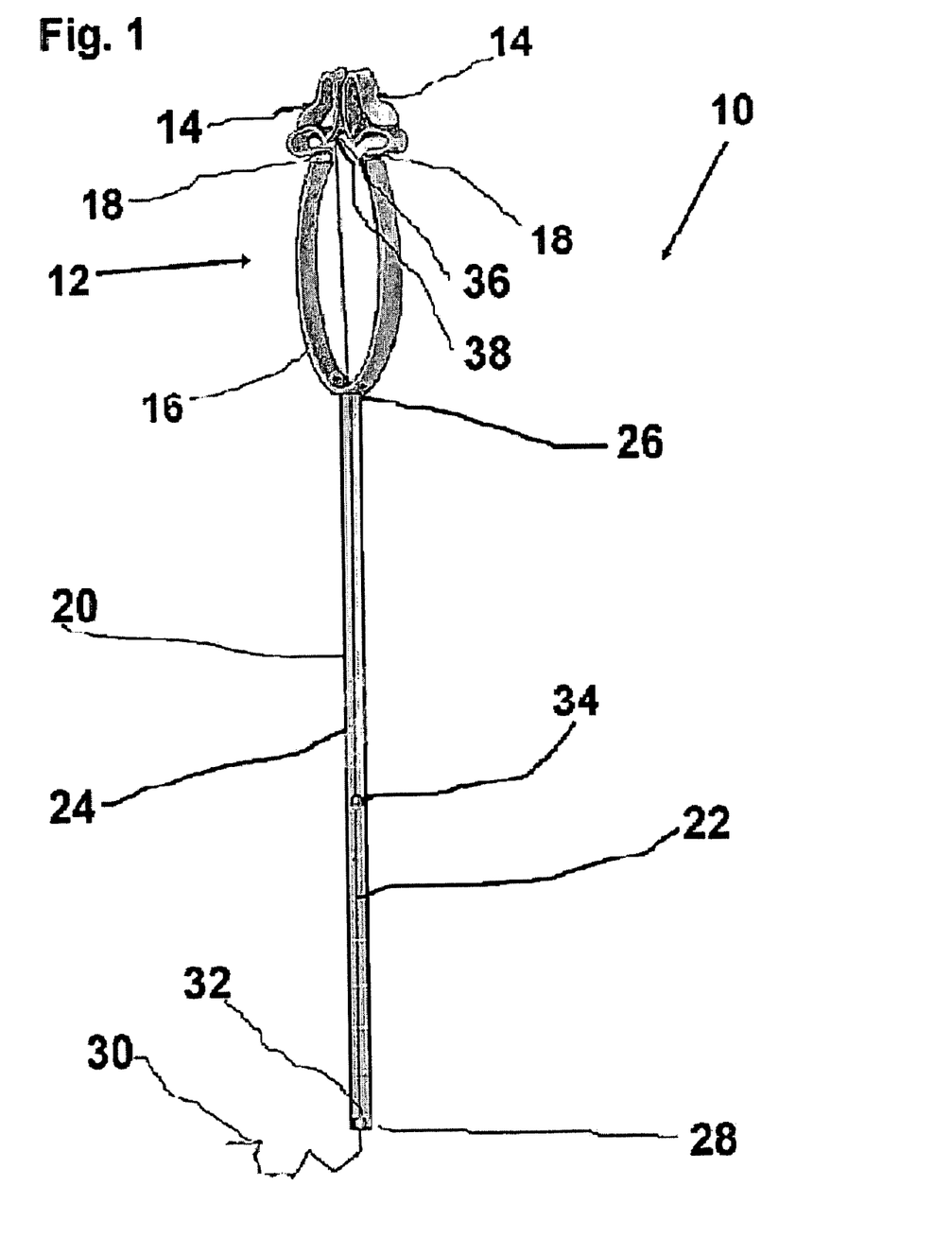
FIG. 1 is an isometric view of a cervical dilation monitor that is constructed and operable in accordance with a preferred embodiment of the invention.
Figure 2:
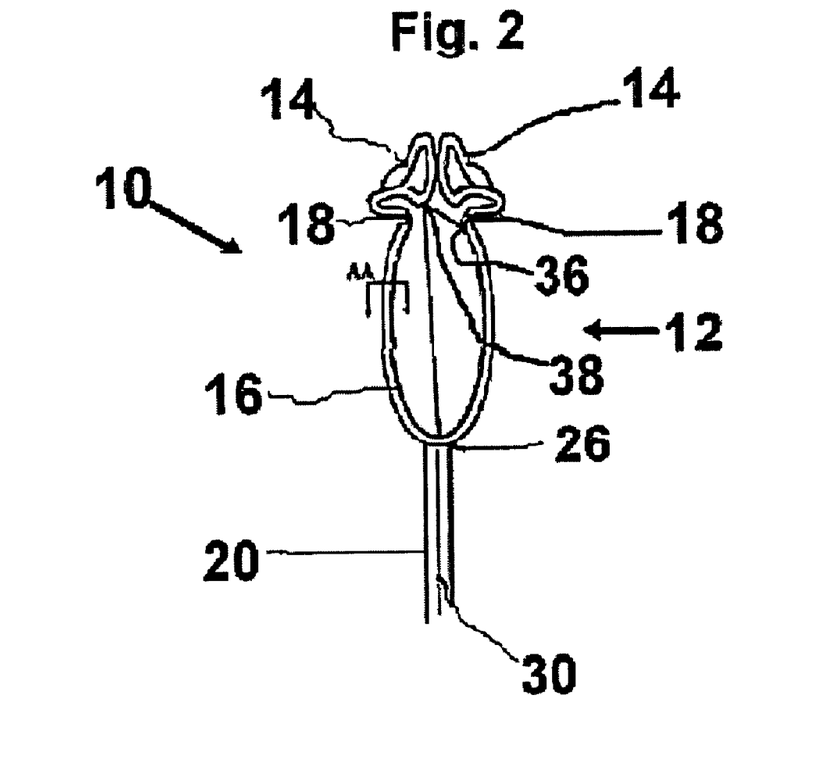
FIG. 2 is a front view of the cervical dilation monitor of FIG. 1.
Figure 3:
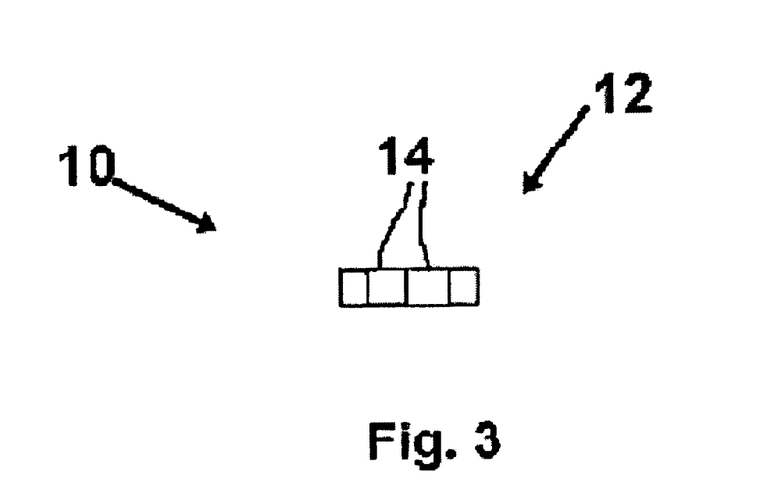
FIG. 3 is a top view of the cervical dilation monitor of FIG. 1.
Figure 4:
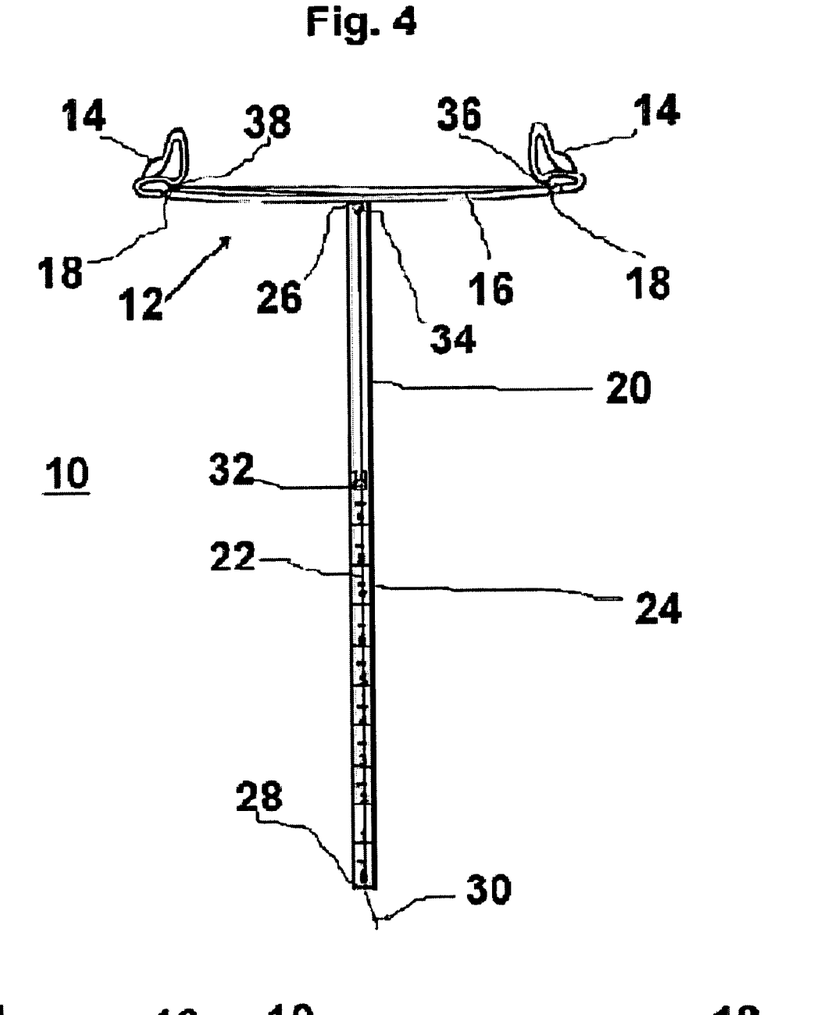
FIG. 4 is a front view of the cervical dilation monitor of FIG. 1 when fully extended.
Figure 5:
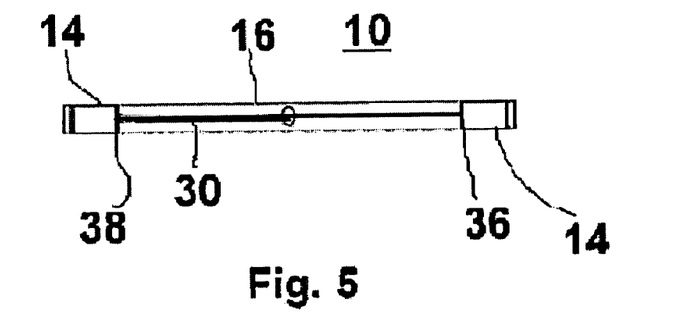
FIG. 5 is a top view of the cervical dilation monitor of FIG. 1 when fully extended.

Reference is now made to FIGS. 1 to 5. FIG. 1 is an isometric view of a cervical dilation monitor 10 that is constructed and operable in accordance with a preferred embodiment of the invention. FIG. 2 is a front view of cervical dilation monitor 10. FIG. 3 is a top view of cervical dilation monitor 10. FIG. 4 is a front view of cervical dilation monitor 10 when fully extended. FIG. 5 is a top view of cervical dilation monitor 10 when fully extended. Cervical dilation monitor 10 includes an expandable gripping arrangement 12 having two oppositely facing gripping members 14 and an outwardly biased restoring member 16. Expandable gripping arrangement 12 is configured, such that, restoring member 16 pushes gripping members 14 apart so that expandable gripping arrangement 12 grips the cervix while the cervix dilates. FIGS. 1, 2 and 3 show cervical dilation monitor 10 in a contracted state, which is generally employed when fitting cervical dilation monitor 10 into a patient, as will be explained later with reference to FIGS. 10 to 12. FIGS. 4 and 5 show cervical dilation monitor 10 in a fully expanded state. Each gripping member 14 is configured to be expandable in order to grip a portion of the cervix even while the cervix effaces, as is best shown with reference to FIGS. 13 to 15. Expandable gripping arrangement 12 includes two flexible connecting elements 18. Each flexible connecting element 18 uniquely mechanically connecting one of gripping members 14 to an end of restoring member 16. Flexible connecting elements 18 enable movement among gripping members 14 and restoring member 16, which is especially important having regard to the changes in the relative position of the dilating cervix, which is gradually moving upward, and gripping members 14.

Figure 6:
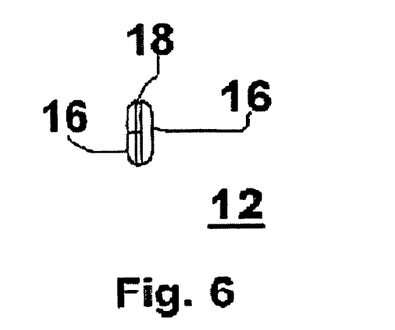
FIG. 6 is a cross-sectional view through the line A—A of FIG. 2.

Reference is now made to FIG. 6, which is a cross-sectional view through the line A—A of FIG. 2. Flexible connecting elements 18 are typically implemented as a single strip of fabric which passes through gripping members 14 (FIG. 2) and restoring member 16. Therefore, expandable gripping arrangement 12 is typically formed by selectively molding biocompatible plastic or silicon on top of a single strip of fabric to form gripping members 14, restoring member 16 and flexible connecting elements 18. Flexible connecting elements 18 is typically formed from a synthetic fabric such as nylon. The fabric typically has a width of between 5 mm to 10 mm. The thickness of gripping members 14 and restoring member 16 is typically between 2 mm to 5 mm.

Reference is again made to FIGS. 1 to 5. Cervical dilation monitor 10 also includes an elongated element 20 having a calibrated scale 22 disposed thereon. Elongated element 20 is generally hollow. Elongated element 20 has a portion 24 which is translucent, typically transparent. Portion 24 also includes calibrated scale 22. Elongated element 20 has two ends, an end 26 and an end 28. End 26 is mechanically connected to approximately the center of restoring member 16. Elongated element 20 is long enough to ensure that calibrated scale 22 is disposed outside of the patient's body. Elongated element 20 is generally formed of clear plastic and is flexible enough to ensure that cervical dilation monitor 10 is not uncomfortable for the patient to use.

Cervical dilation monitor 10 also includes an elongated element 30. It will be appreciated by those skilled in the art that elongated element 30 can be implemented in a number of ways that will perform the function of elongated element 20. However, in accordance with a most preferred embodiment of the present invention elongated element 30 is a line, typically a nylon thread having a thickness typically in the range of 0.5 mm to 2.5 mm. Elongated element 30 is typically 45 cm long. A line includes any equivalent element that will perform the same function as a line, for example, but not limited to, a cord, a cable, a thread, a wire, a string or a ribbon or flexible strip. A part of elongated element 30 is disposed within elongated element 20 along calibrated scale 22. This part of elongated element 30 extends substantially from end 26 to end 28. This part of elongated element 30 has an indicator 32 and a movement restrainer 34 disposed thereon. Indicator 32 and movement restrainer 34 are typically plastic beads, which are mechanically connected to the line forming elongated element 30. Indicator 32 provides an indication of the measured cervical dilation as is explained in more detail below. Movement restrainer 34 prevents elongated element 30 from over extending into the uterus. For example, once cervical dilation monitor 10 is fully extended, movement restrainer 34 prevents any further movement of elongated element 30 as best shown in FIG. 4. Elongated element 20 and elongated element 30 are mechanically connected to expandable gripping arrangement 12, in a manner such that, as expandable gripping arrangement 12 expands with the dilating cervix, relative linear movement is generated between elongated element 20 and elongated element 30, thereby moving indicator 32 with respect to calibrated scale 22 so as to give a measurement of dilation of the cervix. In accordance with the most preferred embodiment of the present invention, the distance moved by indicator 32 is a linear function of the dilation of the cervix.

In accordance with the most preferred embodiment of the present invention, an end 36 of elongated element 30 is typically mechanically connected to one end of restoring member 16. Elongated element 30 is then thread through a loop 38, which is disposed on one gripping member 14. Elongated element 30 is then passed through elongated element 20. Therefore, as the cervix dilates, restoring member 16 pushes gripping members 14 apart, thereby increasing the length of elongated element 30 which is disposed between gripping members 14. Therefore, as the cervix dilates, elongated element 30 and indicator 32 move toward end 26 of elongated element 20. Therefore, the position of indicator 32 with respect to calibrated scale 22 gives a measurement of dilation of the cervix. It will be apparent to those skilled in the art that elongated element 30 can be mechanically connected to expandable gripping arrangement 12 in many ways, for example, but not limited to, mechanically connecting one end of elongated element 30 to one end of restoring member 16 or to one gripping member 14 and by threading elongated element 30 through a loop which is disposed on the other end of restoring member 16 or another gripping member 14.

Figure 7:
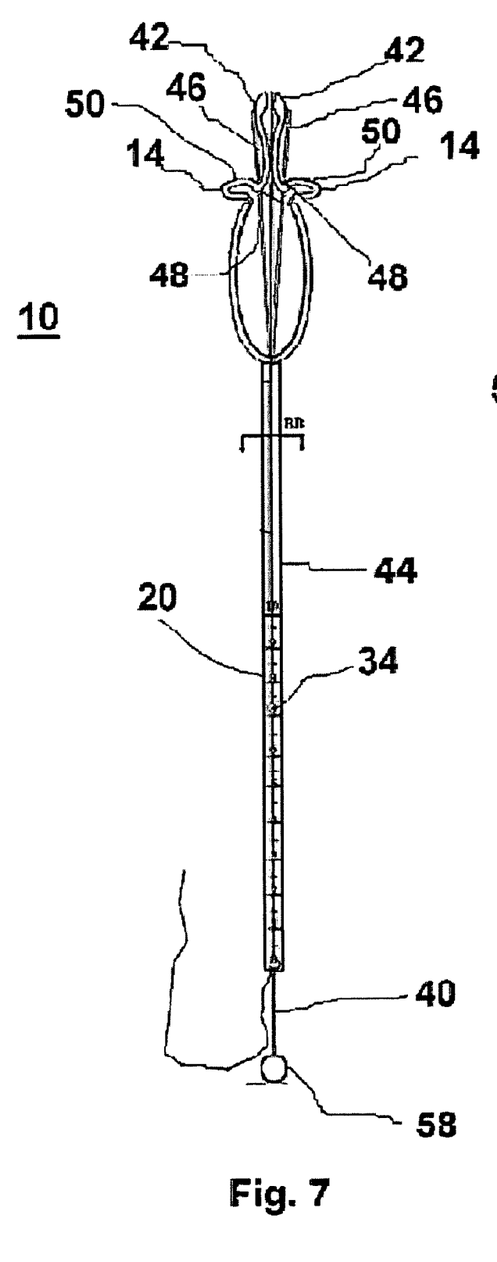
FIG. 7 is a front view of the cervical dilation monitor of FIG. 1 with an insertion arrangement installed.
Figure 8:
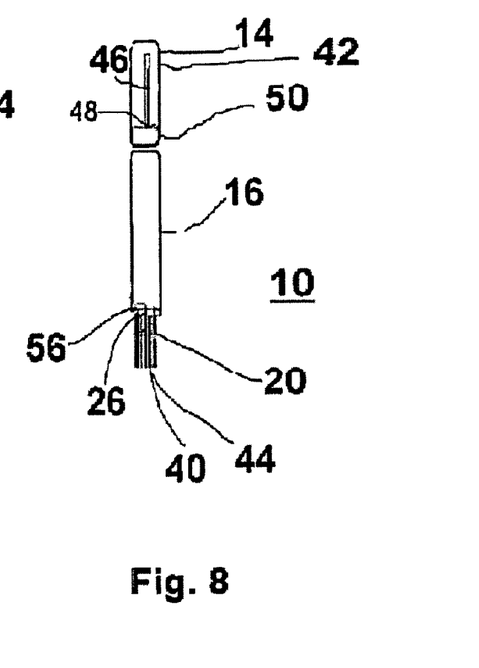
FIG. 8 is a side view of the cervical dilation monitor of FIG. 1 with the insertion arrangement installed.

Reference is now made to FIGS. 7 and 8. FIG. 7 is a front view of cervical dilation monitor 10 of FIG. 1 with an insertion arrangement 40 installed therein. FIG. 8 is a side view of cervical dilation monitor 10 of FIG. 1 with insertion arrangement 40 installed therein. Prior to fitting of cervical dilation monitor 10 onto a dilating cervix, gripping members 14 are expanded, such that the top section 42 of each gripping member 14 is approximately perpendicular with the bottom section 50 of that gripping member 14. Therefore, cervical dilation monitor 10 includes insertion arrangement 40 which is configured to keep gripping members 14 expanded during fitting of expandable gripping arrangement 12 on to the cervix. Insertion arrangement 40 is formed from a rod 44, two arms 46 and a handle 58. Arms 46 are mechanically connected to one end of rod 44 and handle 58 is mechanically connected to the other end of rod 44. Arms 46 are configured, such that, arms 46 have a natural position whereby arms 46 are pushed together. Arms 46 are also configured to be pulled apart as necessary, as will be explained below. Handle 58 is used to help insert and remove insertion arrangement 40 from cervical dilation monitor 10, as will be explained below. Typically, insertion arrangement 40 is formed as a unitary element from plastic. With arms 46 pushed together, insertion arrangement 40 is inserted through elongated element 20. Insertion arrangement 40 is inserted so that arms 46 exit from end 26 of elongated element 20. Each gripping member 14 has a hole 48 disposed therein between top section 42 and bottom section 50. Arms 46 are separated and each arm 46 is uniquely fed through one of holes 48 to support one of top sections 42. Therefore, insertion arrangement 40 is partially disposed within elongated element 20 with arms 46 being disposed outside of elongated element 20. Rod 44 and arms 46 are generally formed as rigid elements. The mechanical connection between rod 44 and arms 46 is rigid enough to keep gripping members 14 expanded by arms 46 supporting top sections 42. Nevertheless, the mechanical connection between rod 44 and arms 46 is flexible enough to enable arms 46 to move apart, and therefore gripping members 14 to move apart, under the action of restoring member 16, which is necessary when cervical dilation monitor 10 is fitted onto a partially dilated cervix, as is described in more detail with reference to FIG. 11. It should be noted that insertion arrangement 40 is typically inserted into cervical dilation monitor 10 as part of the manufacture of cervical dilation monitor 10. Therefore, the cervical dilation monitor 10 is typically supplied ready to use, with insertion arrangement 40 inserted, as well as cervical dilation monitor 10 being sterilized. There is a seal 56 (FIG. 8) which is disposed between end 26 of elongated element 20 and restoring member 16 to prevent movement restrainer 34 (FIG. 7) from exiting elongated element 20 via end 26. End 26 of elongated element 20 is configured to reduce fluid leakage into elongated element 20 by shaping end 26 around restoring member 16.

Figure 9:
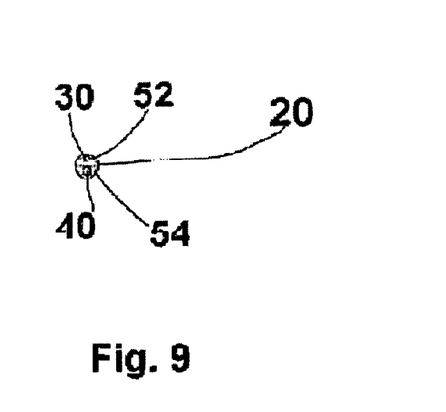
FIG. 9 is a cross-sectional view through the line B—B of FIG. 7.

Reference is now made to FIG. 9, which is a cross-sectional, view through the line B—B of FIG. 7. Elongated element 20 is divided into two sections, a section 52 and a section 54. Section 52 is used for elongated element 30 and section 54 is used for insertion arrangement 40.

Figure 10:
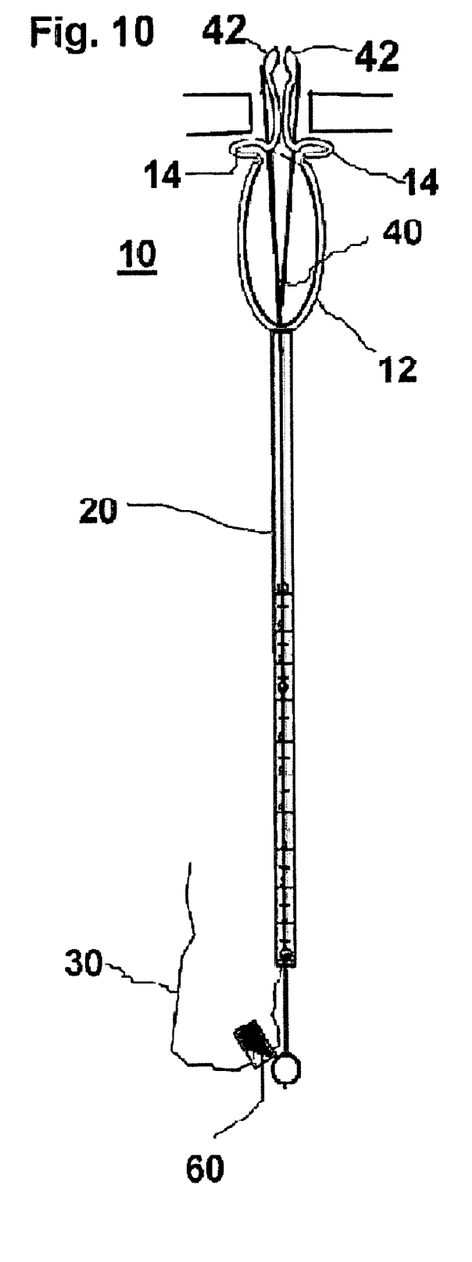
FIG. 10 is a front view of the cervical dilation monitor of FIG. 1 being fitted onto a cervix.
Figure 11:
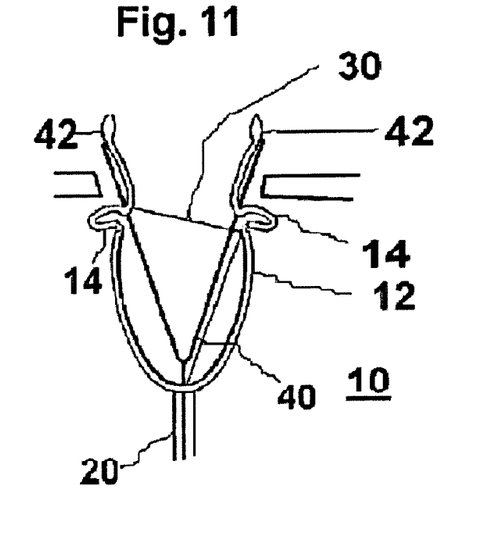
FIG. 11 is a front view of the cervical dilation monitor of FIG. 1 being fitted onto a partially dilated cervix.
Figure 12:
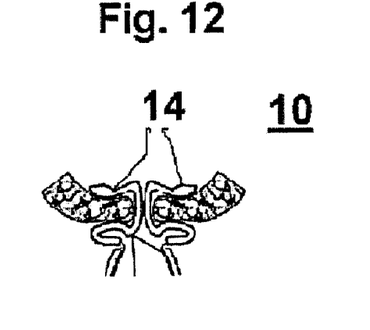
FIG. 12 is a view of the gripping arrangement of the cervical dilation monitor of FIG. 1 after fitting onto a cervix.

Reference is now made to FIGS. 10 and 11. FIG. 10 is a front view of the cervical dilation monitor 10 of FIG. 1 being fitted onto a cervix. FIG. 11 is a front view of cervical dilation monitor 10 of FIG. 1 being fitted onto a partially dilated cervix. Elongated element 30 includes a control element 60 disposed thereon external to elongated element 20 and external to the patient. Control element 60 is typically a clip which is configured to enable an obstetrician to move elongated element 30 in order to contract and expand expandable gripping arrangement 12 for fitting onto the cervix. Control element 60 is configured to be removable from and attachable to elongated element 30, as necessary, in order to clamp elongated element 30 in a certain position without necessitating the obstetrician to constantly hold onto control element 60 or elongated element 30. Additionally, control element 60 provides a grip surface for an obstetrician to pull and release elongated element 30. Prior to insertion of cervical dilation monitor 10 into a patient, expandable gripping arrangement 12 is contracted, typically as part of the manufacture process, by pulling elongated element 30 taught. Insertion arrangement 40 is then inserted into cervical dilation monitor 10, also typically as part of the manufacture process, to keep gripping members 14 expanded. With one hand the obstetrician holds cervical dilation monitor 10 and with the other hand the obstetrician observes the state of the cervix. If the cervix is partially dilated (FIG. 11), elongated element 30 needs to be released slowly until top sections 42 of gripping members 14 come into contact with the wall of the cervix. The obstetrician then slowly removes insertion arrangement 40 from cervical dilation monitor 10, thereby enabling gripping members 14 to contract and grip the cervix, as shown in FIG. 12. Cervical dilation monitor 10 is now fitted and is ready to perform continuous, accurate and objective monitoring of cervical dilation. The monitoring can be easily performed by people other than a physician, such as family of the patient. Moreover, cervical dilation monitor 10 removes the need for repeated vaginal examinations.

Figure 13:
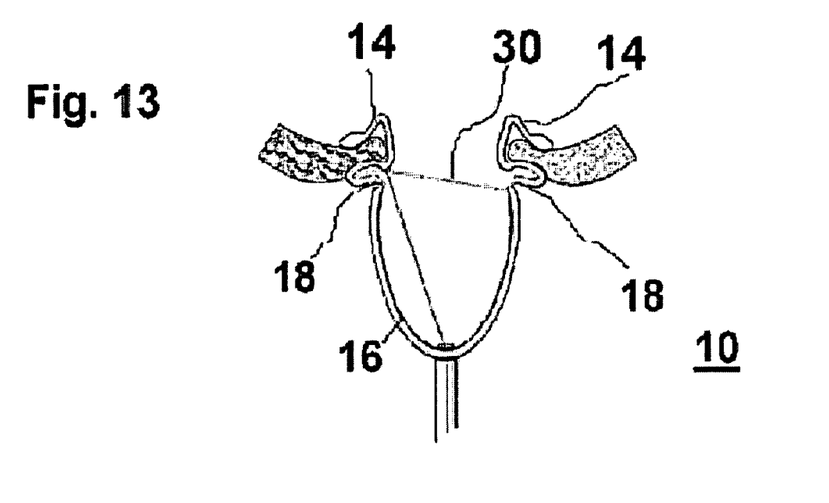
FIG. 13 is a view of the cervical dilation monitor of FIG. 1 after 30 mm dilation of the cervix.
Figure 14:
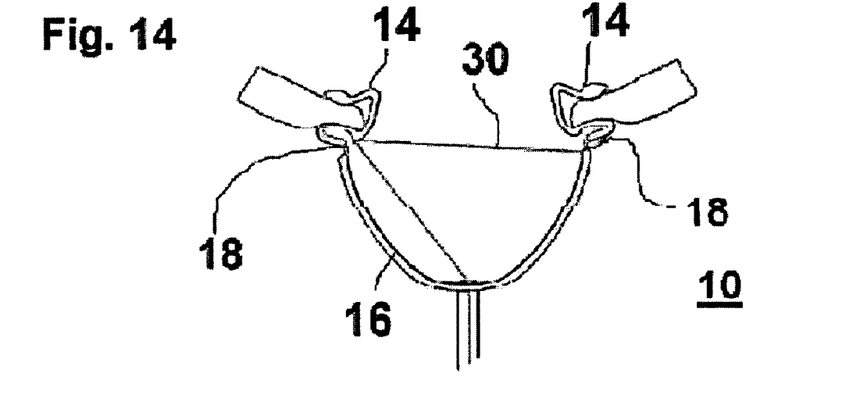
FIG. 14 is a view of the cervical dilation monitor of FIG. 1 after 50 mm dilation of the cervix.
Figure 15:
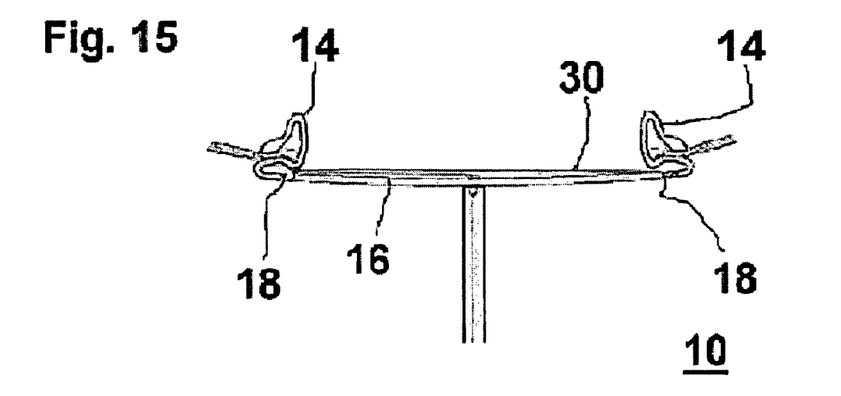
FIG. 15 is a view of the cervical dilation monitor of FIG. 1 after the cervix is fully dilated.

Reference is now made to FIGS. 13, 14 and 15. FIG. 13 is a view of the cervical dilation monitor of FIG. 1 after 30 mm dilation of the cervix. FIG. 14 is a view of the cervical dilation monitor of FIG. 1 after 50 mm dilation of the cervix. FIG. 15 is a view of the cervical dilation monitor of FIG. 1 after the cervix is fully dilated. As discussed above with reference to FIGS. 1 to 5, as the cervix dilates, restoring member 16 pushes gripping members 14 apart so that gripping members 14 continually grip the cervix. Additionally, the length of elongated element 30 which is disposed between gripping members 14 increases as the cervix dilates. Also, flexible connecting elements 18 enable movement among gripping members 14 and restoring member 16 to allow for the shape changes of gripping members 14 and restoring member 16. Additionally, flexible connecting elements 18 enable movement among gripping members 14 and restoring member 16 to allow for the changes in the relative position of the dilating cervix, which is gradually moving upward, and gripping members 14. Additionally, as the cervix dilates it normally also effaces. Therefore, gripping members 14 continually contract to ensure that they hold onto the cervix during dilation and effacement of the cervix.

Figure 16:
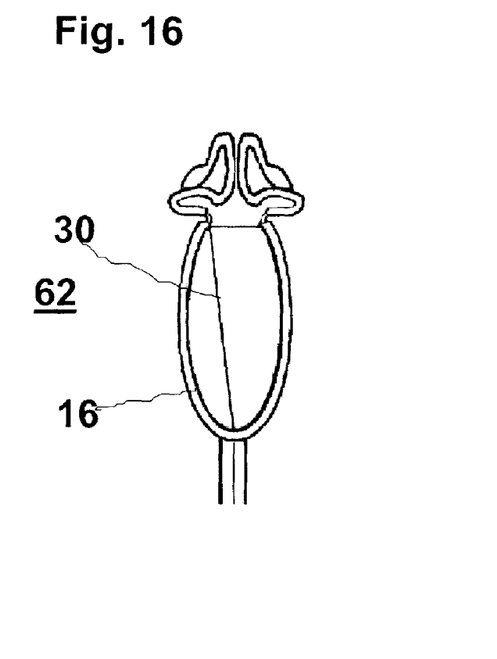
FIG. 16 is a front view of a cervical dilation monitor which is constructed and operable in accordance with a first alternate embodiment of the present invention.

Reference is now made to FIG. 16, which is a front view of a cervical dilation monitor 62 which is constructed and operable in accordance with a first alternate embodiment of the present invention. Cervical dilation monitor 62 is implemented in substantially the same way as cervical dilation monitor 10 (FIG. 1) except that with cervical dilation monitor 62, elongated element 30 is mechanically connected to one end of restoring member 16 and elongated element 30 is then fed through a loop which is disposed on the other end of restoring member 16.

Figure 17:
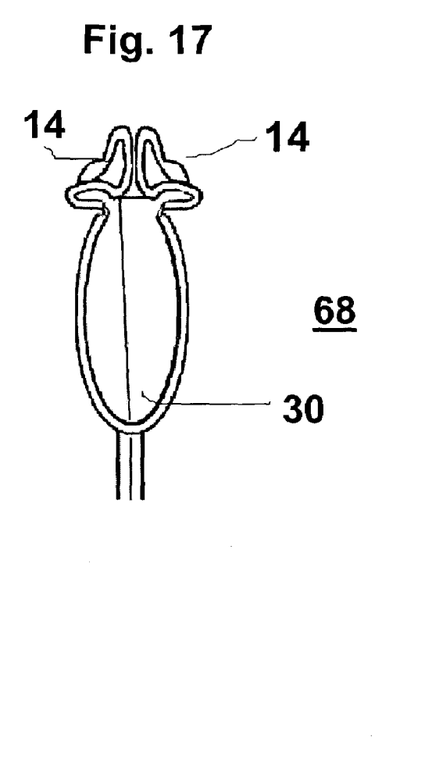
FIG. 17 is a front view of a cervical dilation monitor which is constructed and operable in accordance with a second alternate embodiment of the present invention.

Reference is now made to FIG. 17, which is a front view of a cervical dilation monitor 68 which is constructed and operable in accordance with a second alternate embodiment of the present invention. Cervical dilation monitor 68 is implemented in substantially the same way as cervical dilation monitor 10 (FIG. 1) except that with cervical dilation monitor 68, elongated element 30 is mechanically connected to one gripping member 14 and elongated element 30 is then fed through a loop which is disposed on the other gripping member 14.

Figure 18:
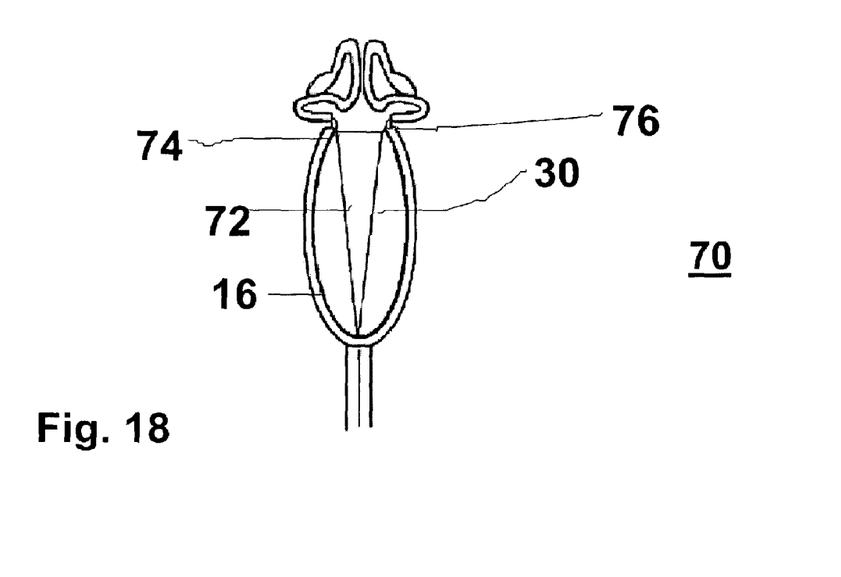
FIG. 18 is a front view of a cervical dilation monitor which is constructed and operable in accordance with a third alternate embodiment of the present invention.

Reference is now made to FIG. 18, which is a front view of a cervical dilation monitor 70 which is constructed and operable in accordance with a third alternate embodiment of the present invention. Cervical dilation monitor 70 is implemented in substantially the same way as cervical dilation monitor 10 (FIG. 1) except that with cervical dilation monitor 70, elongated element 30 forms a closed loop 72 at one end of elongated element 30. The closed loop of elongated element 30 is mechanically connected to restoring member 16 by a loop 74 at one end of restoring member 16 and by another loop 76 at the other end of restoring member 16.

Figure 19:
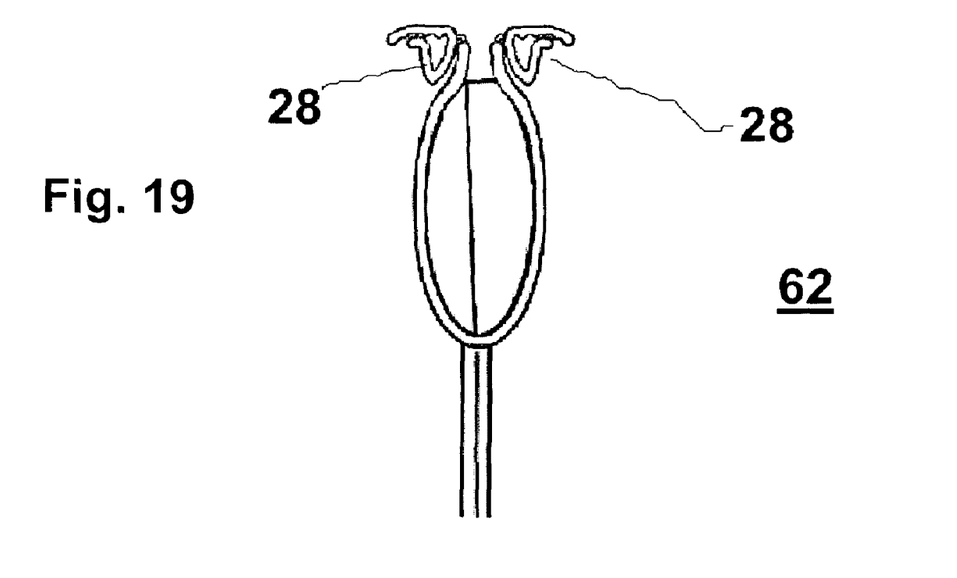
FIG. 19 is a front view of the cervical dilation monitor of FIG. 16 in a contracted state, implemented with a first alternate embodiment of gripping members.
Figure 20:
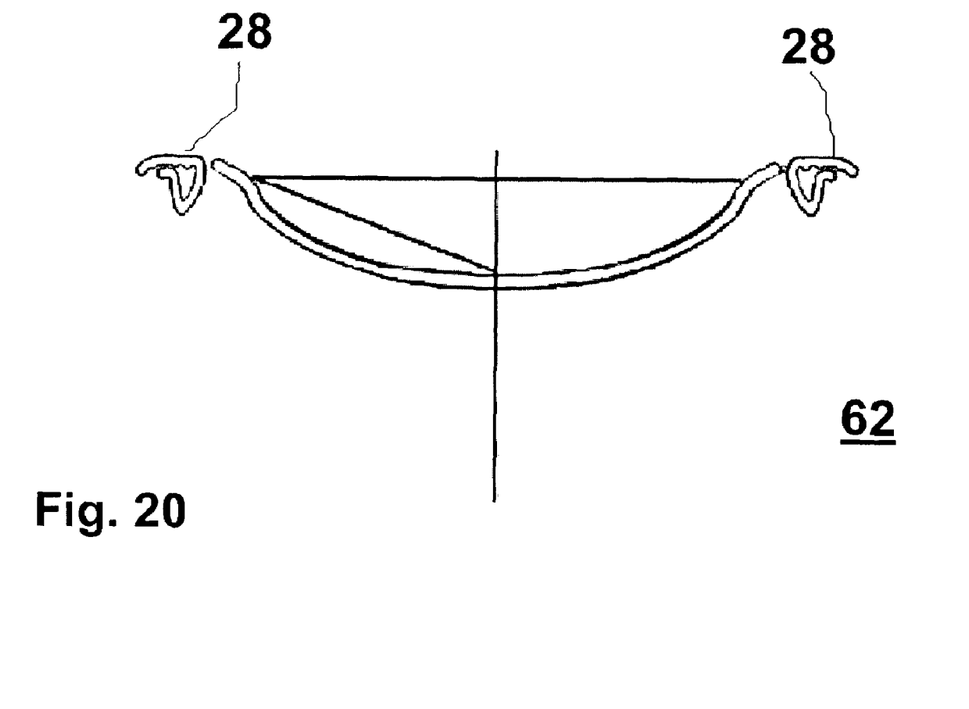
FIG. 20 is a front view of the cervical dilation monitor of FIG. 19 in an expanded state.

Reference is now made to FIGS. 19 and 20. FIG. 19 is a front view of the cervical dilation monitor 62 of FIG. 16 in a contracted state, implemented with a first alternate embodiment of gripping members 78. FIG. 20 is a front view of cervical dilation monitor 62 of FIG. 19 in an expanded state. Gripping members 78 have a profile which is similar to an inverted profile of gripping members 14.

Figure 21:
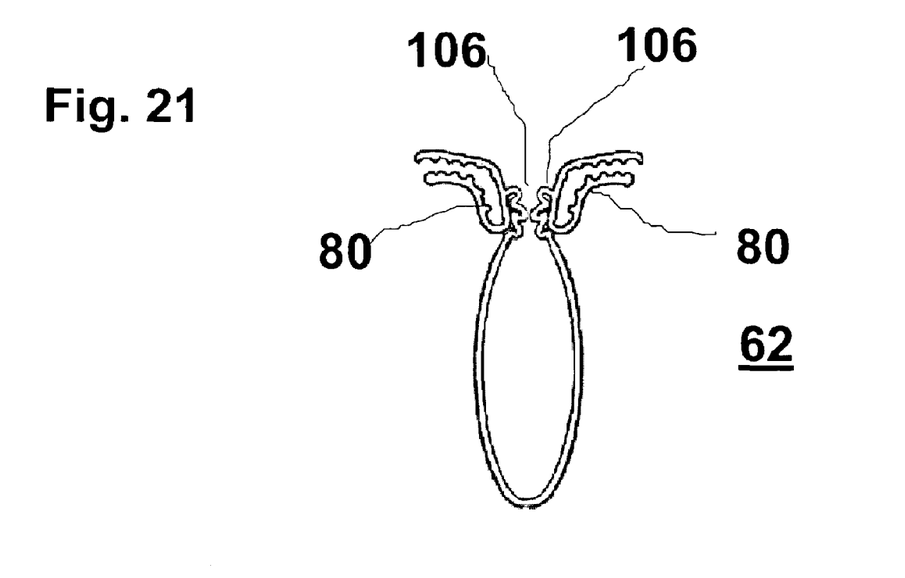
FIG. 21 is a front view of the cervical dilation monitor of FIG. 16 in a contracted state, implemented with a second alternate embodiment of gripping members.
Figure 22:
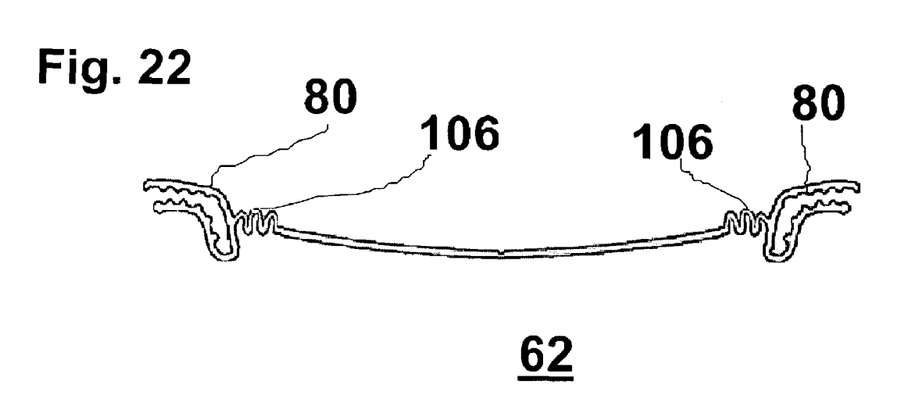
FIG. 22 is a front view of the cervical dilation monitor of FIG. 21 in an expanded state.

Reference is now made to FIGS. 21 and 22. FIG. 21 is a front view of cervical dilation monitor 62 of FIG. 16 in a contracted state, implemented with a second alternate embodiment of gripping members 80. FIG. 22 is a front view of cervical dilation monitor 62 of FIG. 21 in an expanded state. Gripping members 80 provide larger gripping surfaces than gripping members 14. Additionally, restoring member 16 and gripping members 80 do not include an embedded fabric strip, in this embodiment, flexible connecting elements 18 are replaced by two flexible connecting elements 106. Each flexible connecting element 106 is formed from a plastic strip which is bent over itself a number of time in alternate directions.

Figure 23:
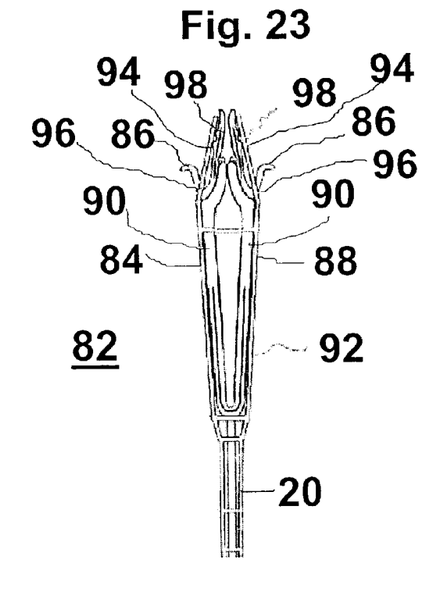
FIG. 23 is a front view of a cervical dilation monitor having an external insertion arrangement that is constructed and operable in accordance with a fourth alternate embodiment of the present invention.
Figure 24:
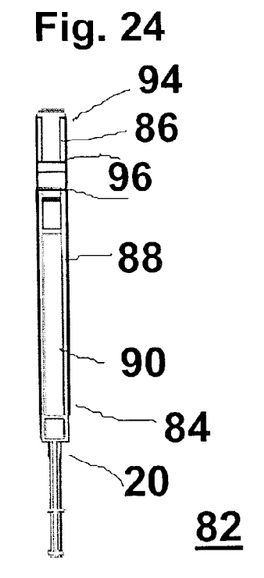
FIG. 24 is a side view of the cervical dilation monitor of FIG. 23.
Figure 25:
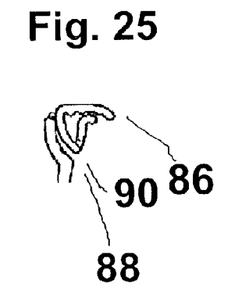
FIG. 25 is a front view of a gripping member of the cervical dilation monitor of FIG. 23 in a contracted state.
Figure 26:
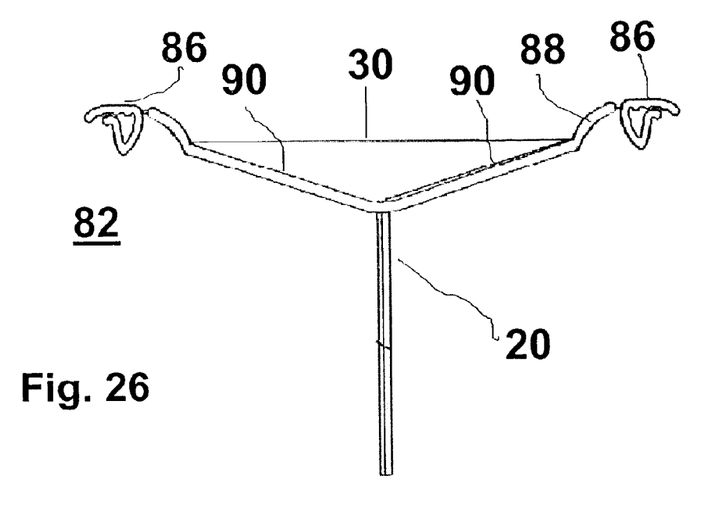
FIG. 26 is a front view of the cervical dilation monitor of FIG. 23 in an expanded state.

Reference is now made to FIGS. 23 to 26. FIG. 23 is a front view of a cervical dilation monitor 82 having an external insertion arrangement 84 that is constructed and operable in accordance with a fourth alternate embodiment of the present invention. FIG. 24 is a side view of cervical dilation monitor 82. FIG. 25 is a front view of a gripping member 86 of cervical dilation monitor 82, gripping member 86 being in a contracted state. FIG. 26 is a front view of cervical dilation monitor 82 without insertion arrangement 84, cervical dilation monitor 82 being in an expanded state. Cervical dilation monitor 82 is implemented in substantially the same way as cervical dilation monitor 10 (FIG. 1) except for the following differences. Cervical dilation monitor 82 has an outwardly biased V-shaped restoring member 88. Restoring member 88 differs from restoring member 16 (FIG. 1) in that restoring member 88 has two arms 90, each arm 90 being rigid and straight for most of its length. Restoring member 88 includes an embedded metal strip 92 (FIG. 23), which is disposed in the central section of restoring member 88, to give restoring member 88 resilience with outward bias. Gripping member 86 has a profile that is an inverted profile of gripping member 14 of cervical dilation monitor 10 (FIG. 1). Each gripping member 86 includes an embedded metal strip 98 (FIG. 23) to give gripping member 86 resilience with inward bias. Elongated element 30 (FIG. 26) is mechanically connected to one end of restoring member 88 and elongated element 30 is fed through a loop which is disposed on the other end of restoring member 88. Insertion arrangement 84 performs the same function as insertion arrangement 40. Insertion arrangement 84 is disposed externally to elongated element 20. Insertion arrangement 84 has two arms 94 which uniquely pass through one of two holes 96 in gripping members 86 to keep gripping members 86 expanded during fitting of cervical dilation monitor 82 onto the cervix.

Figure 27:
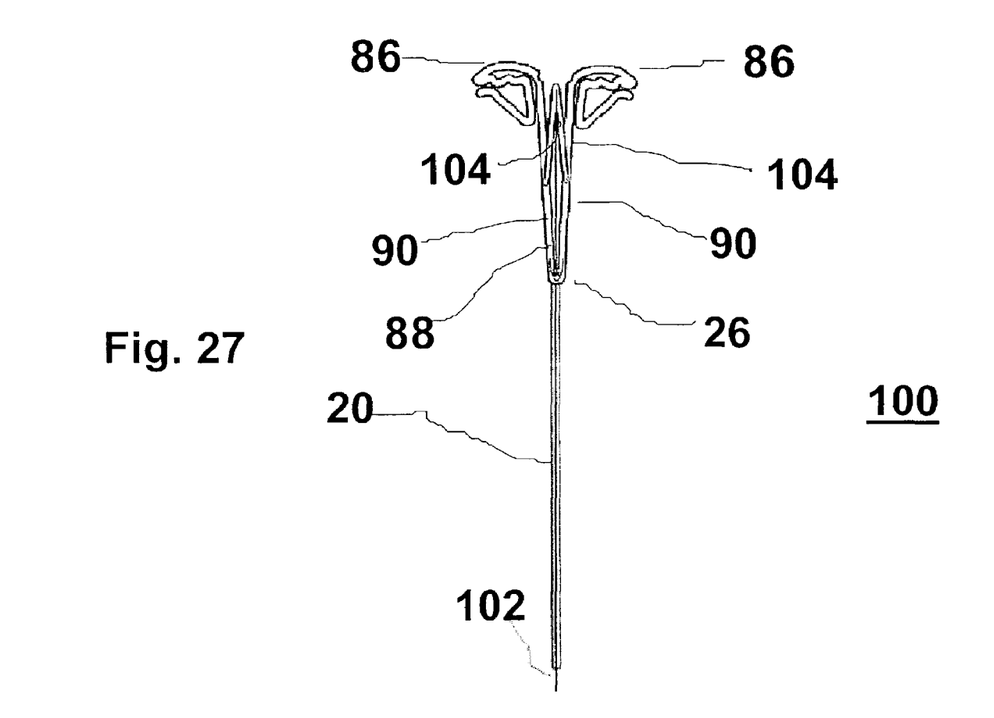
FIG. 27 is a front view of a cervical dilation monitor in a contracted state that is constructed and operable in accordance with a fifth alternate embodiment of the present invention.
Figure 28:
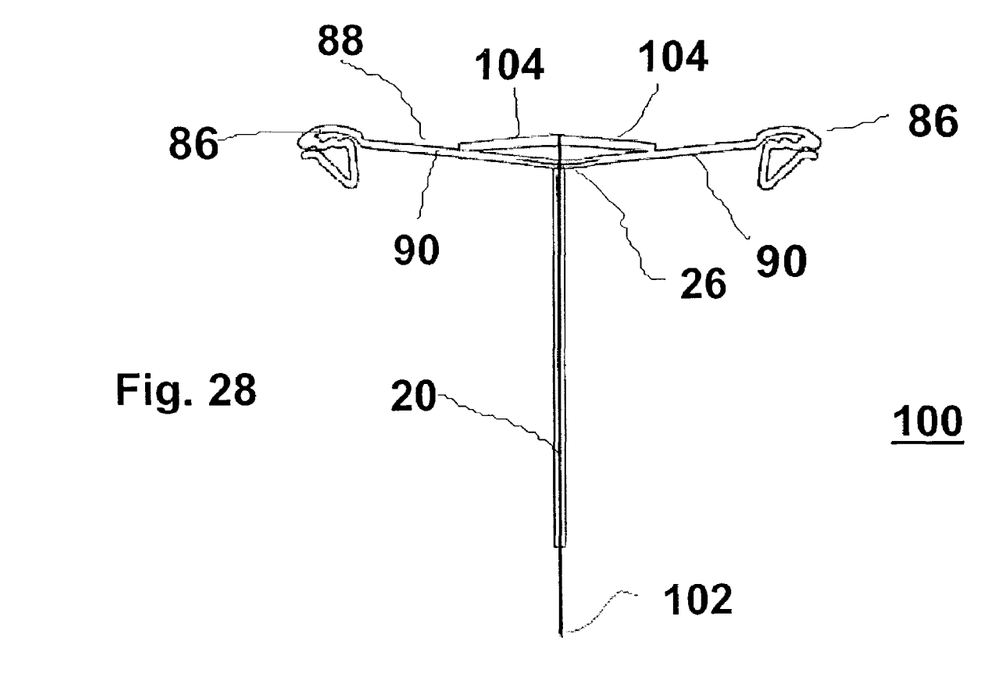
FIG. 28 is a front view of the cervical dilation monitor of FIG. 27 in an expanded state.

Reference is now made to FIGS. 27 and 28. FIG. 27 is a front view of a cervical dilation monitor 100 in a contracted state that is constructed and operable in accordance with a fifth alternate embodiment of the present invention. FIG. 28 is a front view of cervical dilation monitor 100 in an expanded state. Cervical dilation monitor 100 is implemented in substantially the same way as cervical dilation monitor 82 (FIGS. 23 to 26) except for the following differences. Elongated element 30 is replaced by a rigid rod 102 and two rigid arms 104. A part of rod 102 is disposed within elongated element 20. This part of rod 102 has an indicator (not shown) disposed thereon, which is used as a measure of dilation of the cervix against calibrated scale 22 (not shown) on elongated element 20. One end of rod 102 extends out of end 26 of elongated element 20. This end of rod 102 is mechanically connected to one end of arms 104. The other end of one arm 104 is mechanically connected to a central portion of one arm 90 of restoring member 88. The other end of the other arm 104 is mechanically connected to a central portion of the other arm 90. The mechanical connections with arms 104 are configured, such that, arms 104 can swing with respect to the elements connected to arms 104. Therefore, as the cervix expands, restoring member 88 pushes gripping members 86 apart, thereby causing the mechanical connection between arms 104 and rod 102 to move closer to end 26 of elongated element 20. Therefore, as the cervix expands, rod 102 is pushed away from end 26 of elongated element 20. Therefore, the position of the indicator on rod 102 gives a measurement of the dilation of the cervix.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A system for measuring dilation of a cervix of a uterus of a female during the first stage of labor, comprising:
   (a) an expandable gripping arrangement having two oppositely facing gripping members each resiliently biased to a gripping configuration for non-penetrating engagement of the cervix and an outwardly biased restoring member, said gripping arrangement being configured, such that, said restoring member pushes said gripping members apart so that said gripping arrangement grips the cervix while the cervix dilates;
   (b) a first elongated element having a calibrated scale disposed thereon;
   (c) a second elongated element, a part of said second elongated element being disposed along said calibrated scale, said part of said second elongated element having an indicator disposed thereon, said first elongated element and said second elongated element being mechanically connected to said gripping arrangement, in a manner such that, as said gripping arrangement expands with the dilating cervix, relative linear movement is generated between said first elongated element and said part of said second elongated element, thereby moving said indicator with respect to said calibrated scale so as to give a measurement of dilation of the cervix; and
   (d) an insertion arrangement configured to temporarily retain said gripping members in an open configuration during fitting of said gripping arrangement on the cervix and to simultaneously release said gripping members so as to allow said gripping members to return to said gripping configuration for non-penetrating engagement of the cervix.

2. The system of claim 1, wherein said second elongated element is a line.

3. The system of claim 1, wherein at least one of said gripping members is expandable in order to grip a portion of the cervix while the cervix effaces.

4. The system of claim 1, wherein:
   (a) said first elongated element is hollow; and
   (b) said insertion arrangement is partially disposed within said first elongated element.

5. The system of claim 1, wherein said gripping arrangement includes two flexible connecting elements, each of said connecting elements uniquely mechanically connecting one of said gripping members to said restoring member.

6. The system of claim 1, wherein:
   (a) said first elongated element is hollow and has a portion which is translucent, said portion including said calibrated scale; and
   (b) said pair of said second elongated element is disposed within said first elongated element.

7. The system of claim 1, wherein:
   (a) said first elongated element is hollow;
   (b) said first elongated element has a first end and second end;
   (c) said first end is mechanically connected to said restoring member; and
   (d) said second elongated element extends substantially from said first end to said second end.

8. The system of claim 1, wherein said second elongated element has a control element disposed thereon, said control element being configured to enable an operator move said second elongated element to contract said expandable gripping arrangement for fitting into the cervix.

9. The system of claim 1, wherein said second elongated element is mechanically connected to said restoring member and one of said gripping members.

10. The system of claim 1, wherein said second elongated element is mechanically connected to both of said gripping members.

11. A system for measuring dilation of a cervix of a uterus of a female during the first stage of labor, comprising:
    (a) an expandable gripping arrangement including:
       (i) a restoring arrangement including a pair of support arms each having a proximal end and a distal end, said support arms being associated at said proximal ends and being resiliently biased so as to spread apart said distal ends, and
       (ii) two outwardly-facing gripping members each associated with said distal end of one of said elongated support arms, said gripping members being resiliently biased to a gripping configuration for non-penetrating engagement of the cervix;
    (b) a first elongated element having a calibrated scale disposed thereon; and
    (c) a second elongated element, a part of said second elongated element being disposed along said calibrated scale, said part of said second elongated element having an indicator disposed thereon, said first elongated element and said second elongated element being mechanically connected to said gripping arrangement, in a manner such that, as said gripping arrangement expands with the dilating cervix, relative linear movement is generated between said first elongated element and said part of said second elongated element, thereby moving said indicator with respect to said calibrated scale so as to give a measurement of dilation of the cervix.

12. The system of claim 11, wherein said pair of support arms are resiliently flexible.

13. The system of claim 11, wherein at least part of each of said support arms is substantially rigid.

14. The system of claim 11, further comprising an insertion arrangement configured to temporarily retain said gripping members in an open configuration during fitting of said gripping arrangement on the cervix and to release said gripping members so as to allow said gripping members to return to said gripping configuration for non-penetrating engagement of the cervix.

15. The system of claim 14, wherein said insertion arrangement is configured to release said gripping members simultaneously.

* * * * *